(12) United States Patent
Liu et al.

(10) Patent No.: US 10,953,243 B2
(45) Date of Patent: Mar. 23, 2021

(54) RADIATION TREATMENT DEVICE

(71) Applicant: OUR UNITED CORPORATION, Xi'an (CN)

(72) Inventors: Haifeng Liu, Xi'an (CN); Daliang Li, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 0 days.

(21) Appl. No.: 16/815,384

(22) Filed: Mar. 11, 2020

(65) Prior Publication Data

US 2020/0206537 A1 Jul. 2, 2020

Related U.S. Application Data

(63) Continuation of application No. PCT/CN2019/099312, filed on Aug. 5, 2019.

(30) Foreign Application Priority Data

Aug. 24, 2018 (CN) .......................... 201810977447.2

(51) Int. Cl.
*A61N 5/10* (2006.01)

(52) U.S. Cl.
CPC ......... *A61N 5/1049* (2013.01); *A61N 5/1042* (2013.01); *A61N 5/1084* (2013.01);
(Continued)

(58) Field of Classification Search
CPC ...... A61N 5/1049; A61N 5/1077–1084; A61N 2005/1052–1055; A61N 2005/1058; A61N 2005/1061; A61N 2005/1094; A61N 5/1045; A61N 2005/1059; A61N 2005/106; A61N 2005/1062; A61B 6/032–035

See application file for complete search history.

(56) References Cited

U.S. PATENT DOCUMENTS

| 5,259,103 | A | * | 11/1993 | Shepherd | ............. | A61N 5/1084 |
| | | | | | | 29/426.3 |
| 6,438,203 | B1 | * | 8/2002 | Shipeng | ............... | A61N 5/1081 |
| | | | | | | 378/65 |

(Continued)

FOREIGN PATENT DOCUMENTS

| CN | 101541236 A | 9/2009 |
| CN | 102430206 A | 5/2012 |

(Continued)

*Primary Examiner* — Catherine B Kuhlman
(74) *Attorney, Agent, or Firm* — Brion Raffoul

(57) ABSTRACT

The present disclosure discloses a radiation treatment device and pertains to the field of medical appliance technologies. The radiation treatment device includes a radiotherapy unit and an imaging unit. The radiotherapy unit is configured to emit a treatment beam to a to-be-treated region in a patient, wherein the to-be-treated region in the patient is located outside the radiotherapy unit. The imaging unit is arranged adjacent to the radiotherapy unit and is configured to emit an imaging beam to the to-be-treated region in the patient. Without moving the to-be-treated region in a patient, the radiotherapy unit may emit the treatment beam to the to-be-treated region in the patient according to the treatment plan worked out to execute the radiation treatment, such that the accuracy of the radiation treatment is improved.

17 Claims, 6 Drawing Sheets

(52) U.S. Cl.
CPC .............. *A61N 2005/1052* (2013.01); *A61N 2005/1055* (2013.01); *A61N 2005/1057* (2013.01); *A61N 2005/1058* (2013.01); *A61N 2005/1061* (2013.01); *A61N 2005/1094* (2013.01)

(56) References Cited

U.S. PATENT DOCUMENTS

| | | | |
|---|---|---|---|
| 7,502,443 B1 | 3/2009 | Haynes et al. | |
| 2006/0067468 A1* | 3/2006 | Rietzel | A61N 5/1049 378/65 |
| 2008/0317200 A1* | 12/2008 | Lecomte | A61B 6/032 378/19 |
| 2010/0094119 A1* | 4/2010 | Yu | G01R 33/4808 600/411 |
| 2015/0202465 A1* | 7/2015 | Zhao | A61N 5/1077 600/1 |
| 2019/0015686 A1* | 1/2019 | Yu | A61N 5/1084 |

FOREIGN PATENT DOCUMENTS

| | | | |
|---|---|---|---|
| CN | 203694431 U | * | 7/2014 |
| CN | 203694431 U | | 7/2014 |
| CN | 106163613 A | | 11/2016 |
| CN | 108635687 A | | 10/2018 |

\* cited by examiner

RADIATION TREATMENT DEVICE

CROSS REFERENCE TO RELATED APPLICATIONS

The present disclosure is a continuation of international application No. PCT/CN2019/099312, filed on Aug. 5, 2019, which claims priority to the Chinese application No. 201810977447.2, filed on Aug. 24, 2018, both are hereby incorporated by reference in its entireties.

BACKGROUND

At present, to improve the speed and accuracy for tumor localization and radiation treatment, radiation treatment devices routinely combine radiotherapy units and imaging units, such that radiation treatment can be performed on patients without moving the patients from imaging rooms equipped with the imaging units to treatment rooms equipped with the radiotherapy units, and the radiation treatment procedures are as follows.

A patient is initially moved to an imaging unit by moving a treatment couch to complete tumor imaging, and a treatment plan is subsequently worked out based on the size and shape of the tumor in the images as well as surrounding tissues, etc. Next, the patient is moved to the radiotherapy unit by moving the treatment couch, and the treatment couch is properly located such that the tumor location corresponds to the tumor location in the treatment plan, and finally, the radiation treatment is executed for the tumor in the patient.

However, the treatment couch needs to be relocated before the radiation treatment device performs the radiation treatment on the tumor in the patient, which may lead to a location error of the treatment couch and thus may have a negative effect on the accuracy of the radiation treatment. Moreover, the imaging unit and the radiotherapy apparatus in the radiation treatment device cannot work simultaneously, and thus it is impossible to perform image-guided radiation treatment on the patient, particularly the patient subject to the radiation treatment.

SUMMARY

To solve the above technical problems, embodiments of the present disclosure provide a radiation treatment device, which may improve the accuracy of radiation treatment and may perform image-guided radiation treatment on a patient in real time.

To achieve an objective of the present disclosure, an embodiment of the present disclosure provides a radiation treatment device, which includes a radiotherapy unit and an imaging unit. The radiotherapy unit is configured to emit a treatment beam to a to-be-treated region in a patient, and the to-be-treated region in the patient is located outside the radiotherapy unit. The imaging unit is arranged adjacent to the radiotherapy unit and is configured to emit an imaging beam to the to-be-treated region in the patient.

Compared with related technologies, the radiation treatment device in the embodiments of the present disclosure includes a radiotherapy unit and an imaging unit. The radiotherapy unit is configured to emit a treatment beam to a to-be-treated region in a patient, wherein the to-be-treated region in the patient is located outside the radiotherapy unit. The imaging unit is arranged adjacent to the radiotherapy unit and is configured to emit an imaging beam to the to-be-treated region in the patient.

The radiotherapy unit also may emit a treatment beam to the same to-be-treated region. That is, the radiotherapy unit and the imaging unit have the same projection target, i.e., the to-be-treated region. Therefore, without moving the to-be-treated region in the patient, the radiotherapy unit may emit the treatment beam to the to-be-treated region in the patient according to a treatment plan worked out to execute the radiation treatment, such that the accuracy of the radiation treatment is improved.

Furthermore, in the process of the radiation treatment, the radiation treatment device can perform imaging while perform treatment, and can perform real-time image-guided radiation treatment on the to-be-treated region in the patient, so as to ensure the to-be-treated region to always correspond to the location in the treatment plan.

BRIEF DESCRIPTION OF THE DRAWINGS

The accompanying drawings are provided for further understanding the technical solutions of the present disclosure and constitute a part of the specification, and, together with the embodiments of the present disclosure, are provided to interpret the technical solutions of the present disclosure, rather than limiting the technical solutions of the present disclosure.

DETAILED DESCRIPTION OF THE EMBODIMENTS

Detailed description of embodiments of the present disclosure will be made below with reference to the accompanying drawings to make the objectives, technical solutions and advantages of the present disclosure more apparent.

It is to be noted that the embodiments of the present disclosure and the features in the embodiments may be arbitrarily combined with each other on a non-conflict basis.

Figure 1:
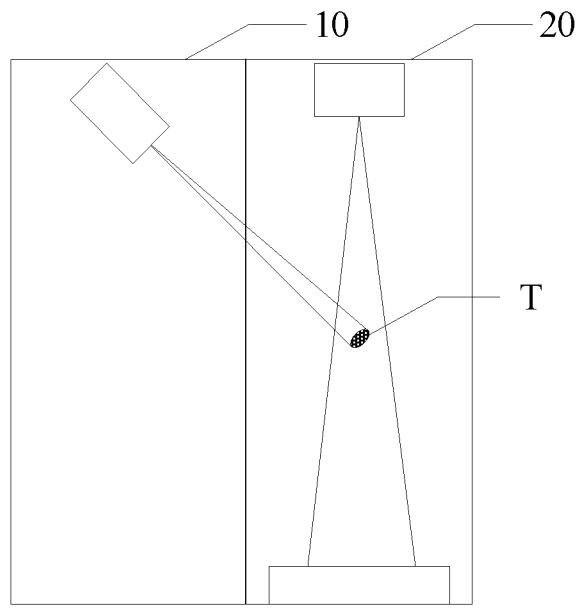
FIG. 1 is a schematic side view I of a radiation treatment device according to an embodiment of the present disclosure.

FIG. 1 is a schematic side view of a radiation treatment device according to an embodiment of the present disclosure. As shown in FIG. 1, the radiation treatment device includes a radiotherapy unit 10 and an imaging unit 20. The radiotherapy unit 10 is configured to emit a treatment beam to a to-be-treated region T in a patient, wherein the to-be-treated region T in the patient is located outside the radiotherapy unit 10. The imaging unit 20 is arranged adjacent to the radiotherapy unit 10 and is configured to emit an imaging beam to the to-be-treated region T in the patient.

The radiation treatment device in the embodiments of the present disclosure emits an imaging beam to the to-be-treated region T in the patient by using the imaging unit 20 to obtain an image of the to-be-treated region T in the patient. A treatment plan is worked out on the basis of the image of the to-be-treated region T in the patient. The radiotherapy unit 10 also may emit a treatment beam to the same to-be-treated region T. That is, the radiotherapy unit 10 and the imaging unit 20 have the same projection target, i.e., the to-be-treated region T. Therefore, without moving the to-be-treated region T in the patient, the radiotherapy unit 10 may emit the treatment beam to the to-be-treated region T in the patient according to the treatment plan worked out to execute the radiation treatment, such that the accuracy of the radiation treatment is improved.

Furthermore, in the process of the radiation treatment, the radiation treatment device may perform imaging while performing treatment, and may perform real-time image-guided radiation treatment on the to-be-treated region T in the patient, so as to ensure the to-be-treated region T to always correspond to the treatment location in the treatment plan.

In the embodiments of the present disclosure, the radiotherapy unit 10 may be an intensity modulated radiation treatment apparatus, a cyberknife (x-ray knife), or a multi-source focused radiation treatment apparatus, etc. The imaging unit 20 may be at least one of the apparatuses that follow: an X-ray apparatus, a cone beam CT (CBCT) apparatus, a computed tomography (CT) apparatus, a magnetic resonance imaging (MRI) apparatus, a positron emission computed tomography (PET) apparatus, an ultrasound apparatus, or a digital subtraction angiography (Digital Subtraction Angiography, DSA) apparatus.

Figure 2:
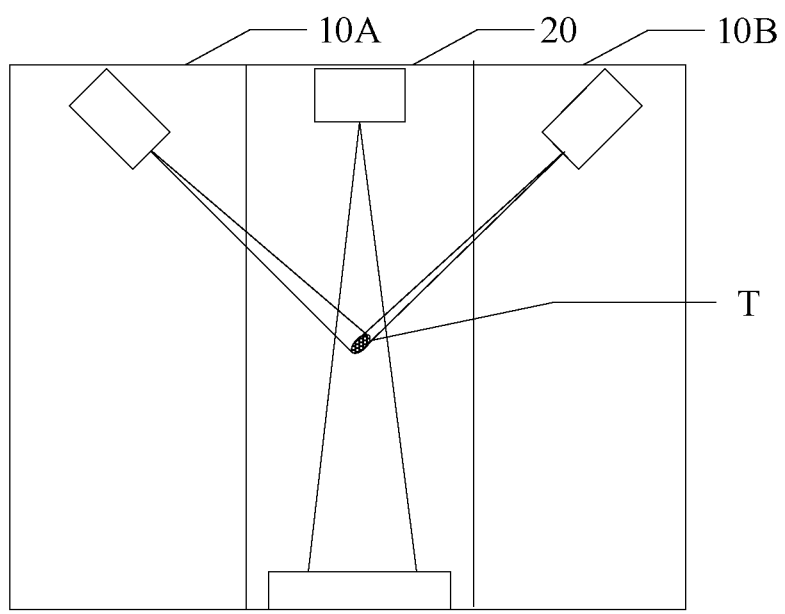
FIG. 2 is a schematic side view II of another radiation treatment device according to an embodiment of the present disclosure.

Further, there may be a plurality of radiotherapy units 10. As shown in FIG. 2, the radiotherapy unit 10 may include a first radiotherapy unit 10A and a second radiotherapy unit 10B. The imaging unit 20 is located between the first radiotherapy unit 10A and the second radiotherapy unit 10B. The first radiotherapy unit 10A and the second radiotherapy unit 10B may simultaneously emit treatment beam to the to-be-treated region T to improve the efficiency of the radiation treatment.

Figure 3:
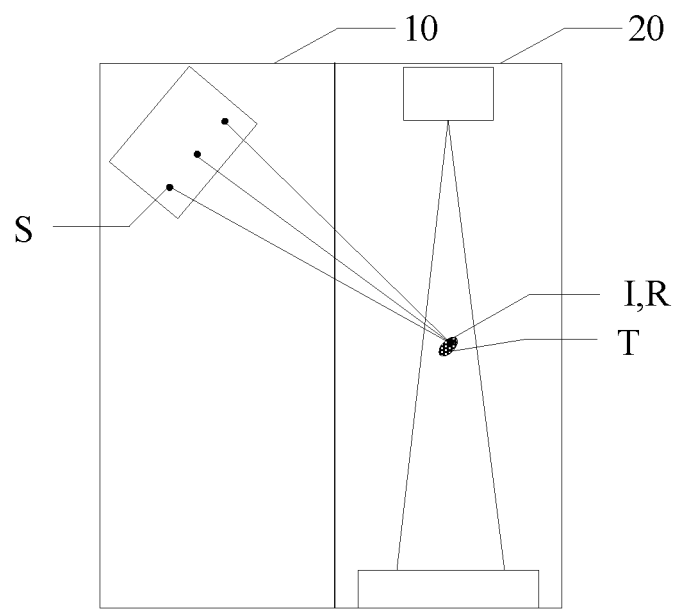
FIG. 3 is a schematic side view III of a radiation treatment device according to an embodiment of the present disclosure.

When the radiotherapy unit 10 is the multi-source focused radiation treatment apparatus, as shown in FIG. 3, the radiotherapy unit 10 includes a plurality of radioactive sources S. The treatment beams emitted by the plurality of radioactive sources S are focused at an intersection point I outside the radiotherapy unit 10, and the intersection point I coincides with an imaging center R of the imaging unit 20. It is to be readily understood that when there are two radiotherapy units 10, the first radiotherapy unit 10A and the second radiotherapy unit 10B each include a plurality of radioactive sources S. The treatment beams emitted by the plurality of radioactive sources S are focused at an intersection point I outside the radiotherapy unit 10, and the intersection point I coincides with an imaging center R of the imaging unit 20.

It is to be understood that the to-be-treated region T may include one or more to-be-treated targets, and each time the radiation treatment is performed, the intersection point I where the plurality of treatment beams are focused coincides with one of the targets.

Figure 4:
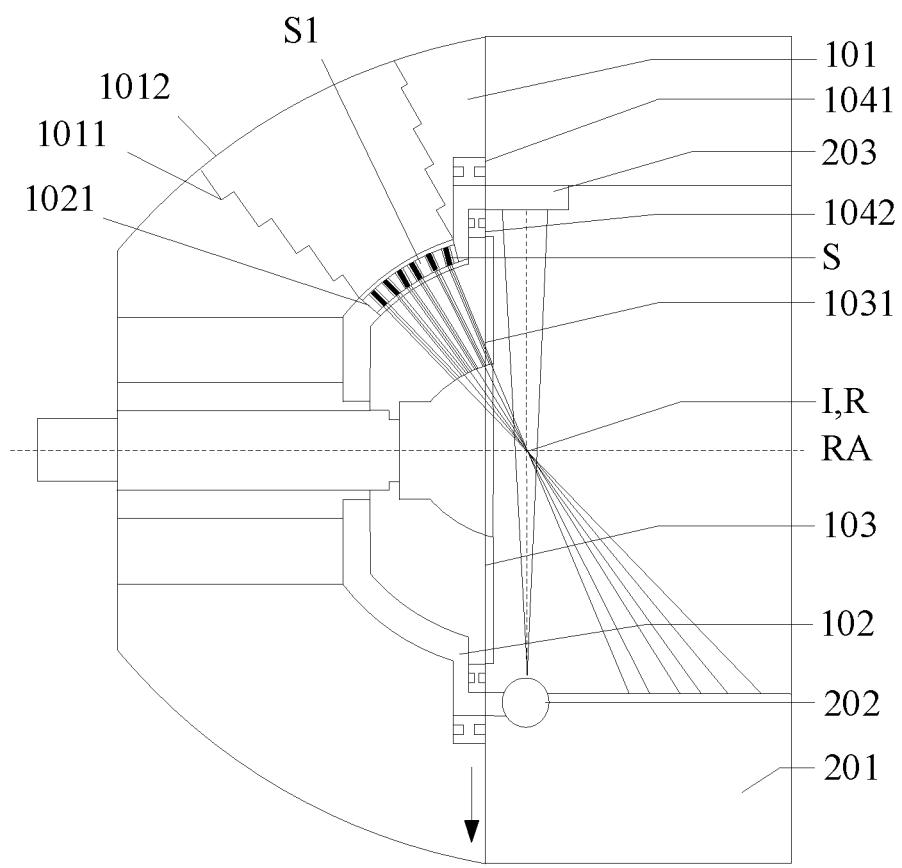
FIG. 4 is a schematic side view IV of a radiation treatment device according to an embodiment of the present disclosure.
Figure 5:
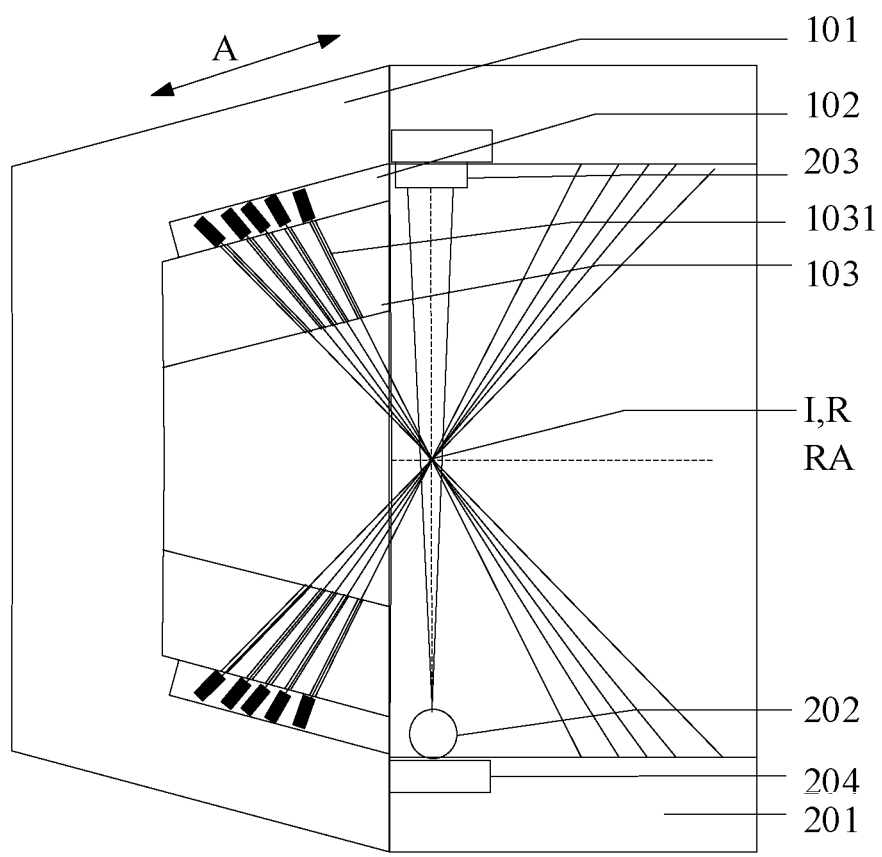
FIG. 5 is a schematic side view V of a radiation treatment device according to an embodiment of the present disclosure.

Further, as shown in FIG. 4 and FIG. 5, the radiotherapy unit 10 includes a shield body 101, a source body 102, and a collimator 103 in sequence from outside to inside. The shield body 101 is configured to shield rays, the source body 102 is configured to carry the plurality of radioactive sources S, and the collimator 103 has a collimation channel 1031. When the collimation channel 1031 of the collimator 103 is aligned with the plurality of radioactive sources S, that is, when the radioactive sources S are turned on, the treatment beams emitted by the plurality of radioactive sources S may be focused at the intersection point I through the collimation channel 1031 to treat the targets in the patient. When the collimation channel 1031 of the collimator 103 is not aligned with the plurality of radioactive sources S, that is, when the plurality of radioactive sources S are turned off, the treatment beams emitted by the plurality of radioactive sources S are shielded by the collimator 103, and the radiation treatment device stops the treatment. Here, the intersection point I coincides with the imaging center R of the imaging unit 20.

The shield body 101 of the radiotherapy unit 10 generally is made of a shielding material such as lead or tungsten. The radiotherapy unit 10 has a large total weight. Due to the action of gravity, as shown in FIG. 4, the radiotherapy unit 10 may sag in the direction (the direction of arrow in FIG. 4) perpendicular to a rotation axis RA. Therefore, a first anti-sagging component 1041 is arranged between the shield body 101 and the source body 102, and a second anti-sagging component 1042 is arranged between the source body 102 and the collimator 103 to prevent the radiotherapy unit 10 from sagging as a whole. Further, the above anti-sagging components may be annular bearings, such as rolling bearings, etc.

To align or not align the collimation channel 1031 of the collimator 103 with a plurality of radioactive sources S, that is, to turn on or off the radioactive sources, at least two possible examples below may be adopted.

In a possible example, as shown in FIG. 4, the source body 102 in the radiotherapy unit 10 does not rotate about the rotation axis RA, whereas the collimator 103 rotates about the rotation axis RA. The rotation of the collimator 103 causes the collimation channel 1031 of the collimator 103 to be aligned or not aligned with the plurality of radioactive sources S. Similarly, the source body 102 may be designed to rotate about the rotation axis RA, but the collimator 103 does not rotate about the rotation axis RA. Of course, the source body 102 and the collimator 103 may be designed to rotate about the rotation axis RA in different rotation directions or at different rotation speeds.

When the collimation channel 1031 of the collimator 103 is aligned with the plurality of radioactive sources S, if the source body 102 and the collimator 103 rotate together about the rotation axis RA, rays (treatment beams) emitted by the radioactive sources S irradiate the target at different angles, which may prevent normal tissues around the target from being exposed to ray irradiation for a long time.

In another possible example, as shown in FIG. 5, the source body 102 in the radiotherapy unit 10 does not move along a preset trajectory A, whereas the collimator 103 moves along the predetermined trajectory A. The movement of the collimator 103 causes the collimation channel 1031 of the collimator 103 to be aligned or not aligned with the plurality of radioactive sources S. Similarly, the source body 102 may be designed to move along the predetermined trajectory A, whereas the collimator 103 does not move along the predetermined trajectory A. Of course, the source body 102 and the collimator 103 may be designed to move along the predetermined trajectory A in different movement directions or at different movement speeds.

It is to be noted here that the first example is described taking a bowl-shaped radiotherapy unit 10 as an example, and the second example is described taking a tube-shaped radiotherapy unit 10 as an example. Of course, the radiotherapy unit 10 may have other structures, and the shape or the like of the radiotherapy unit 10 is not specifically limited in the embodiments of the present disclosure.

For ease of installation or replacement of the radioactive source, a bowl-shaped radiotherapy unit 10 is taken as an example. As shown in FIG. 4, the radioactive source S may be arranged on a source case Si. Accordingly, the source body 102 includes a source case mounting hole 1021, and the source case Si is mounted in the source case mounting hole 1021. Further, the shield body 101 includes a source case shield hole 1011 and a source case shield block 1012, wherein a size of the source case shield hole 1011 is greater than or equal to a size of the source case mounting hole 1021, and the source case shield block 1012 matches the source case shield hole 1011.

In addition, the above-mentioned radioactive sources S may be uniformly distributed in a spiral shape on the source body 102, or may be divided into a plurality of groups, which are all distributed on a sector of the source body 102. Each group of radioactive sources is distributed in the direction of the rotation axis RA, or each group of radioactive sources is uniformly distributed in a circle of an annular shield member 201 of the source body 102.

No matter the radioactive source is turned on or off in whatever way, the treatment beam passing through the intersection point I may leak out. Therefore, as shown in FIG. 4 and FIG. 5, the imaging unit 20 includes a shield member 201 arranged adjacent to the radiotherapy unit 20 and configured to shield the treatment beam passing through the intersection point I. After a treatment beam emitted from the radioactive source S passes through the intersection point I, the treatment beam may be shielded by the shield member 201, which effectively prevents rays from leaking out in the treatment process.

The above-mentioned shield member 201 is hollow-shaped (for example, ring-shaped) or sheet-shaped (for example, C-shaped). When the shield member 201 is sheet-shaped, the shield member 201 may rotate with the radioactive source S at any time to shield the rays (treatment beams) emitted by the radioactive source S. However, the thickness of the shield member 201, the size of a hollow-shaped intermediate opening, and the size of the sheet may be set according to the direction and intensity of the treatment beam passing through the intersection point I.

Further, the imaging unit 20 also includes an imaging source 202 and an imager 203. In a possible example, as shown in FIG. 4, the imaging source 202 and the imager 203 are arranged opposite to each other on an end surface at an edge of the source body 102 or the collimator 103 rotatable about the rotation axis RA, and the imaging source 202 and the imager 203 may rotate with the source body 102 or the collimator 103. In another possible example, as shown in FIG. 5, the imaging source 202 and the imager 203 are oppositely arranged on a rotation ring 204 in the shield member 201 and are rotatable about the rotation axis RA. In other possible examples, there are at least two groups of imaging sources 202 and imagers 203 in the imaging unit 20, which are arranged oppositely inside the shield member 201 respectively, and a preset angle (such as 90 degrees) is formed between the two groups of imaging sources 202 and imagers 203.

Figure 6:
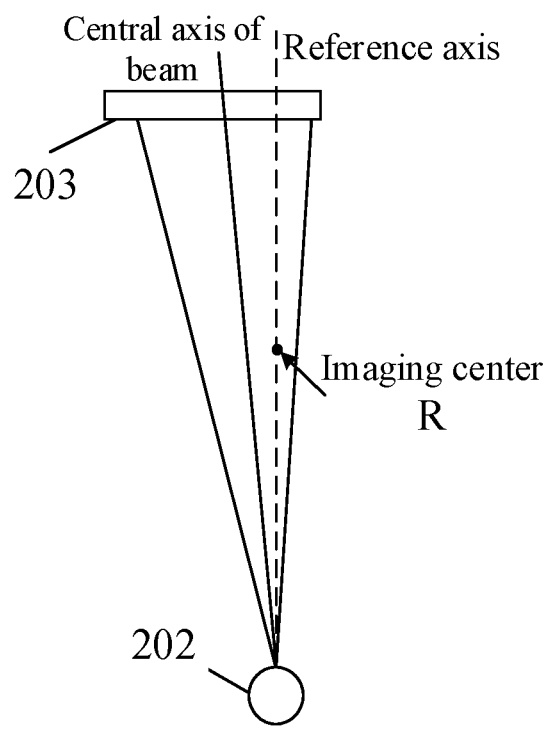
FIG. 6 is a schematic diagram showing a relationship between a central axis of an imaging beam and a reference axis according to an embodiment of the present disclosure.

Further, to increase an imaging volume, as shown in FIG. 6, a central axis of an imaging beam emitted from the imaging source 202 deviates from a reference axis, and the reference axis is an axis penetrating through the imaging center R and perpendicular to the imager 203. When the imaging unit 20 (for example, the imaging source 202 and the imager 203) rotates with the radiotherapy unit 20, the imaging beam may form a larger imaging volume.

Figure 7:
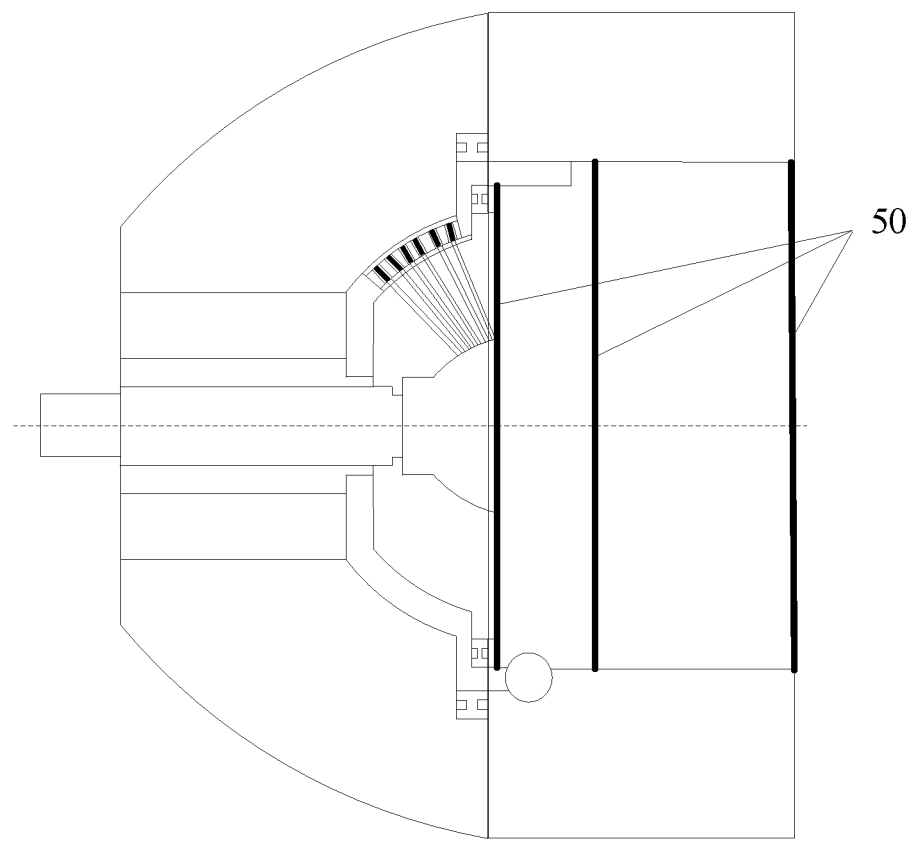
FIG. 7 is a schematic diagram showing a mounted position of a shield door according to an embodiment of the present disclosure.

Further, the radiation treatment device also includes a shield door 50 configured to open or close the radiation treatment device, or to shield the treatment beam emitted from the radiotherapy unit 10. Taking the bowl-shaped radiotherapy unit 10 as shown in FIG. 3 as an example, as shown in FIG. 7, the shield door 50 may be arranged at an exit of the treatment beam from the radiotherapy unit 10 or inside the imaging unit 20 or outside the imaging unit 20. When the radiation treatment device is not in operation, if beams emitted by the radioactive source S are not completely shielded by the collimator 103, the shield door 50 may be configured to shield these unshielded rays. If the beams emitted by the radioactive source S are completely shielded by the collimator 103, the shield door 50 may be configured to open or close therapeutic space of the radiation treatment device. Of course, the shield door 50 may be configured to shield these unshielded rays and may also be configured to open or close the therapeutic space of the radiation treatment device.

Figure 8:
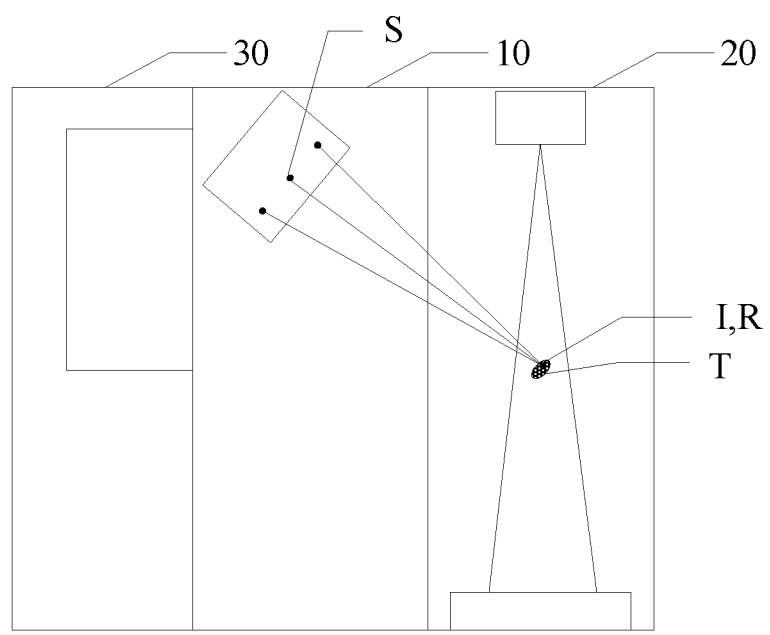
FIG. 8 is a schematic side view VI of a radiation treatment device according to an embodiment of the present disclosure.

When the radiotherapy unit 10 in the above embodiment is of a partial shield design, to prevent the radioactive source S from leaking out when the radiotherapy unit 10 is not in use, as shown in FIG. 8, the radiation treatment device further includes a radioactive source receiving unit 30 configured to receive and store the radioactive source S into the radioactive source receiving unit 30 when the radiotherapy unit 10 is not in operation.

Figure 9:
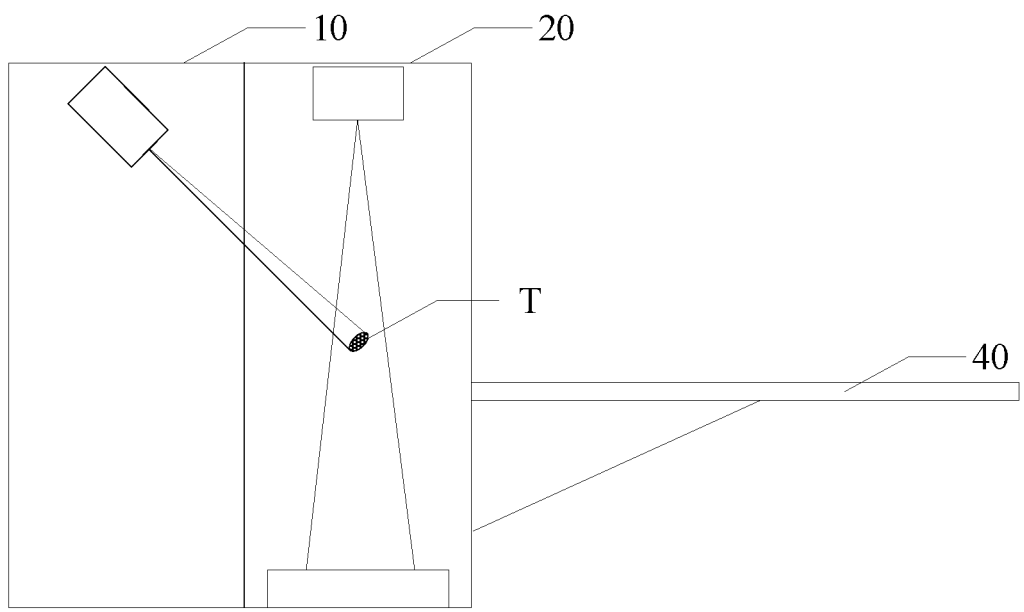
FIG. 9 is a schematic side view VII of a radiation treatment device according to an embodiment of the present disclosure.

As shown in FIG. 9, the radiation treatment device further includes a treatment couch 40 arranged at a side of the imaging unit 20. The treatment couch 40 may be a three-dimension couch or a six-dimension couch.

The above is merely for the convenience of understanding the technical solution of the present disclosure by those skilled in the art, and is not intended to limit the present disclosure. All modifications, equivalent substitutions and improvements made within the spirit and principle of the present disclosure shall fall within the protection scope of the present disclosure.

What is claimed is:
1. A radiation treatment device, consisting essentially of:
   an imaging unit comprising:
      a first end and a second end along a rotational axis;
      a first opening at the first end adapted to receive a patient;
      an imaging source;
      an imager arranged opposite the imaging source, the imaging source and the imager being rotatable about the rotational axis and defining an imaging center; and
      a shield member; and
   a single radiotherapy unit adjacent to the second end of the imaging unit, the radiotherapy unit comprising:
      a bowl-shaped source body carrying radioactive sources; and
      a bowl-shaped collimator having collimation channels, the collimation channels permitting treatment beams emitted by the radioactive sources to be projected inside the imaging unit and focused at an intersection point overlapping the imaging center in the imaging unit;

the bowl-shaped source body and the bowl-shaped collimator arranged concentric about the rotational axis, and closing a second opening at the second end;

the shield member arranged adjacent to the radiotherapy unit for shielding the treatment beams passing through the intersection point.

2. The radiation treatment device according to claim 1, wherein the radiotherapy unit further comprises a shield body, the shield body abutting the second end of the imaging unit.

3. The radiation treatment device according to claim 2, wherein the shield body comprises a source case shield hole for mounting a source case shield block.

4. The radiation treatment device according to claim 3, further comprising a source case, wherein the radioactive sources are arranged in the source case.

5. The radiation treatment device according to claim 2, further comprising a first annular bearing between the shield body and the source body.

6. The radiation treatment device according to claim 5, further comprising a second annular bearing between the source body and the collimator.

7. The radiation treatment device according to claim 1, wherein the radioactive sources are distributed in a sector of the source body.

8. The radiation treatment device according to claim 1, wherein the radioactive sources are distributed evenly on the source body.

9. The radiation treatment device according to claim 1, wherein a central axis of an imaging beam emitted from the imaging source deviates from a reference axis passing through the imaging center and perpendicular to the imager.

10. The radiation treatment device according to claim 1, wherein the imaging unit comprises at least one of:
an X-ray apparatus, a cone beam CT (CBCT) apparatus, a computed tomography (CT) apparatus, a magnetic resonance imaging (MRI) apparatus, a positron emission computed tomography (PET) apparatus, an ultrasound apparatus, or a digital subtraction angiography (DSA) apparatus.

11. The radiation treatment device according to claim 1, further comprising a shield door at the first end to shield the treatment beam emitted from the radiotherapy unit.

12. The radiation treatment device according to claim 1, further comprising a shield door at the second end.

13. The radiation treatment device according to claim 1, further comprising a treatment couch arranged at the first end of the imaging unit.

14. The radiation treatment device according to claim 1, wherein the imaging source and the imager are arranged on an end surface at an edge of the source body, and rotate with the source body.

15. The radiation treatment device according to claim 1, wherein the imaging source and the imager are arranged on an end surface at an edge of the collimator, and the imaging source and the imager rotate with the collimator.

16. The radiation treatment device according to claim 1, wherein the imaging source and the imager are arranged on a rotation ring.

17. The radiation treatment device according to claim 1, wherein the imaging unit is a cone beam CT (CBCT) apparatus.

* * * * *